(12) United States Patent
Yamazaki

(10) Patent No.: US 10,828,159 B2
(45) Date of Patent: Nov. 10, 2020

(54) METHOD OF REPAIRING AORTIC VALVE

(71) Applicant: SUN MEDICAL TECHNOLOGY RESEARCH CORPORATION, Nagano (JP)

(72) Inventor: Kenji Yamazaki, Hokkaido (JP)

(73) Assignee: SUN MEDICAL TECHNOLOGY RESEARCH CORPORATION, Nagano (JP)

( * ) Notice: Subject to any disclaimer, the term of this patent is extended or adjusted under 35 U.S.C. 154(b) by 48 days.

(21) Appl. No.: 16/208,517

(22) Filed: Dec. 3, 2018

(65) Prior Publication Data
US 2020/0170797 A1 Jun. 4, 2020

(51) Int. Cl.
*A61F 2/24* (2006.01)
*A61B 17/04* (2006.01)
*A61B 17/00* (2006.01)

(52) U.S. Cl.
CPC ........ *A61F 2/2442* (2013.01); *A61B 17/0469* (2013.01); *A61F 2/2415* (2013.01); *A61B 2017/00243* (2013.01); *A61F 2/2427* (2013.01); *A61F 2220/0075* (2013.01)

(58) Field of Classification Search
CPC .... A61F 2/2442; A61F 2/0469; A61F 2/2415; A61F 2/2451; A61F 2/2448
See application file for complete search history.

(56) References Cited

U.S. PATENT DOCUMENTS

2014/0288594 A1* 9/2014 Shaefers ................. A61L 17/10
606/222
2016/0317302 A1* 11/2016 Madjarov ............. A61F 2/2445

OTHER PUBLICATIONS

Kenji Minakata, MD et al., "Is repair of aortic valve regurgitation a safe alternative to valve replacement?", The Journal of Thoracic and Cardiovascular Surgery, vol. 127, No. 3, pp. 645-653, 9pp.

* cited by examiner

*Primary Examiner* — Tan-Uyen T Ho
*Assistant Examiner* — Lee O Chedister
(74) *Attorney, Agent, or Firm* — Hauptman Ham, LLP (57) ABSTRACT

A method of repairing an aortic valve includes, in a following order: an aortic wall incision step; an aortic valve forming step; and an aortic wall suturing step. In the aortic wall incision step, an aortic wall is cut so as to expose an aortic valve side in the inside of an aortic duct to an open atmosphere. In the aortic valve forming step, the aortic valve is formed by restricting a distance between commissures disposed adjacently to each other by placing a thread between the plurality of commissures disposed adjacently to each other. In the aortic wall suturing step, the aortic wall cut in the aortic wall incision step is sutured so as to close the aortic wall.

5 Claims, 11 Drawing Sheets

-- Prior Art --

-- Prior Art --

FIG.11C

-- Prior Art --

METHOD OF REPAIRING AORTIC VALVE

BACKGROUND OF THE INVENTION

1. Field of the Invention

The present invention relates to a method of repairing an aortic valve.

2. Description of the Related Art

To treat diseases relating to an aortic valve (an aortic stenosis, an aortic regurgitation and the like) "a prosthetic valve replacement surgery" has been performed conventionally. In the prosthetic valve replacement surgery, a patient's own valve is replaced with a prosthetic valve such as a mechanical valve or a bioprosthetic valve. Lives of many patients have been saved by this prosthetic valve replacement surgery.

However, the prosthetic valve replacement surgery also has drawbacks.

The mechanical valve is manufactured using an artificial material. In this case, blood is liable to adhere to the valve so that thrombus is liable to occur. Accordingly, a patient has to keep taking an anticoagulant such as warfarin for preventing the occurrence of thrombus. This compulsory medicine taking imposes a large burden on the patient. In the case where a dosage of an anticoagulant is excessively large, when a patient suffers from an external injury, bleeding of blood cannot be easily stopped thus giving rise to a bleeding risk. In view of the above, it is necessary to take a countermeasure such as constant monitoring of a state of blood and adjustment of a dosage when necessary.

On the other hand, when a patient's own valve is replaced with a bioprosthetic valve, it is unnecessary for the patient to take an anticoagulant. However, the bioprosthetic valve is deteriorated with a lapse of time such as hardening or the like and hence, the bioprosthetic valve has a drawback with respect to its durability.

To prevent the occurrence of such drawbacks, depending on cases, treatment by "valvuloplasty" (valve repair operation) which does not use a prosthetic valve has been performed (for example see Kenji Minakata, MD et al., "Is repair of aortic valve regurgitation a safe alternative to valve replacement?", The Journal of Thoracic and Cardiovascular Surgery, Vol.127, Number 3, pp. 645-653). Valvuloplasty is treatment where a patient's own aortic valve is repaired by making use of his own valve without removing his own aortic valve.

Figure 11A:
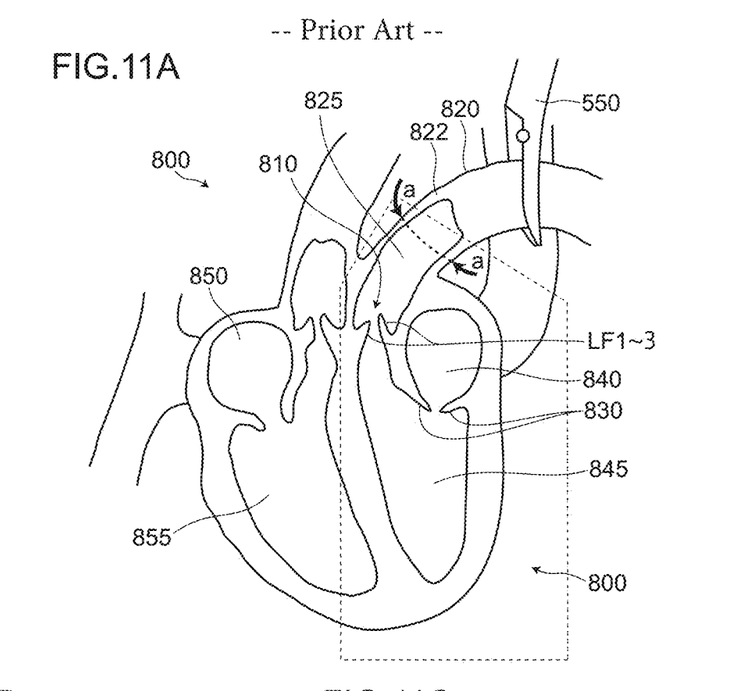
FIG. 11A is a view for describing an aortic wall incision step which is performed prior to repairing of the valve.
Figure 11B:
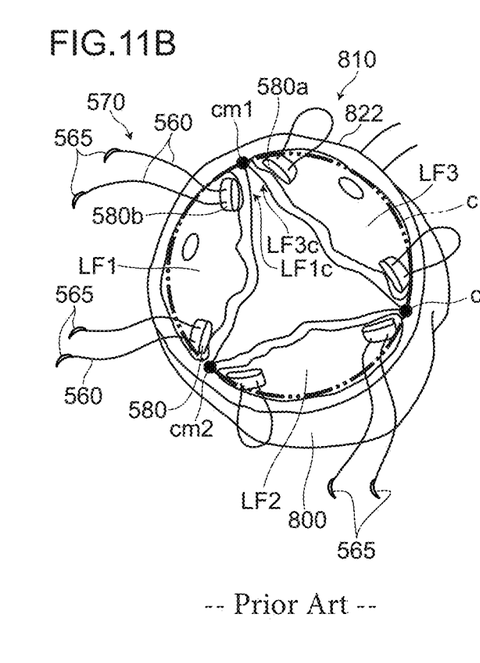
Figure 11C:
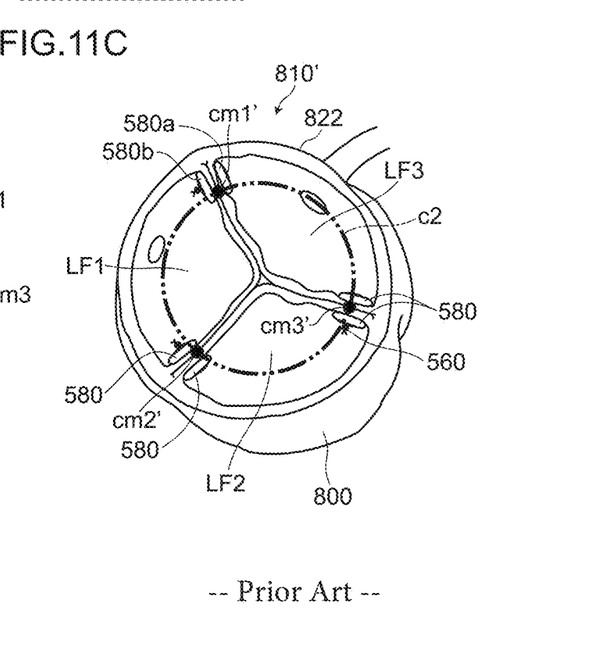

FIG. 11A to FIG. 11C are views for describing a conventional method of repairing an aortic valve. FIG. 11A is a view for describing an aortic wall incision step which is performed prior to forming of the valve. In the drawing, among parts which form a heart 800, a left atrium 840, a left ventricle 845, a right atrium 850, a right ventricle 855, and surrounding of these parts are shown in cross section. Symbol 550 indicates an aortic cross clamp, and symbol 830 indicates a mitral valve respectively. FIG. 11B and FIG. 11C are views for describing forming of the valve. The respective drawings show modes where an aortic valve 810 is viewed in a direction substantially perpendicular to an incision surface (cutting surface) when an aortic wall 822 is cut. Double dashed chain lines indicated by symbols c1 and c2 respectively indicate a circumferential length of an aortic annulus imaginarily described.

The conventional valvuloplasty is performed in accordance with the following steps (conventional method of repairing an aortic valve), for example, although the steps depend on cases.

(1) The aortic wall 822 is cut at a suitable portion (an incision portion a-a indicated by an arrow in FIG. 11A, for example) of an aorta 820, and an aortic valve 810 side of the inside of an aortic duct 825 is exposed to an open atmosphere (aortic wall incision step).

(2) Forming of the aortic valve is performed in the vicinity of "commissure" which is a portion where cusps disposed adjacently to each other abut against each other and are joined to each other (commissure forming step).

For example, hereinafter, the case is described where the aortic valve is formed at a portion in the vicinity of a first commissure cm1 where a third cusp LF3 and a first cusp LF1 are abut against each other and are joined to each other. Firstly, a double armed suture 570 is made to penetrate a pledget 580a in advance. Then, needles 565 of the double armed suture 570 are made to pierce the third cusp LF3, and the needles 565 and threads 560 are made to penetrate the first cusp LF1. In a first cusp LF1 side, the needles 565 and the threads 560 are made to penetrate another pledget 580b (see FIG. 11B). Then, the threads 560 are tied to each other by fastening on the first cusp LF1 side.

Through such steps, a tissue LF1c of the first cusp LF1 on a side close to the first commissure cm1 and a tissue LF3c of the third cusp LF3 on a side close to the first commissure cm1 are pulled together while catching a wall portion of the aortic wall 822, and are fixed in a state where the tissues LF1c and LF3c are sandwiched by the pledget 580a and the pledget 580b (see FIG. 11C) (first commissure forming step).

The above-mentioned steps may be performed in the same manner also at the second commissure cm2 where the first cusp LF1 and the second cusp LF2 abut against each other and are joined to each other and the third commissure cm3 where the second cusp LF2 and the third cusp LF3 abut against each other and are joined to each other.

(3) Cut aortic wall 822 is sutured so as to close the aortic wall 822 (not shown in the drawing) (aortic wall suturing step).

According to the conventional method of repairing an aortic valve, the substantial positions of the commissures can be corrected from the positions indicated by cm1, cm2, cm3 shown in FIG. 11B to the positions indicated by cm1', cm2', cm3' in FIG. 11C. In other words, distances between a plurality of commissures (inter-commissure distances) can be substantially shortened and hence, a substantial circumferential length of the aortic annulus can be shortened from c1 in FIG. 11B to c2 in FIG. 11c.

Accordingly, the cusps disposed adjacently to each other (particularly free edges of such cusps) can be made close to each other and hence, a gap between the cusps disposed adjacently to each other (a gap at a center portion of the aortic valve 810) can be eliminated whereby the prevention of aortic regurgitation is improved.

SUMMARY OF INVENTION

However, a possibility cannot be denied that a geometric relationship between the commissures collapses due to enlargement of an inter-commissure distance due to various circumstances after an operation. As a result, a case is considered where a gap is formed between cusps disposed adjacently to each other thus inducing aortic regurgitation (AR) or the like again.

The present invention has been made in view of the above-mentioned circumstances, and it is an object of the present invention to provide a method of repairing an aortic valve where a geometric relationship between a plurality of commissures can be normalized and the normalized state can be maintained.

A method of repairing an aortic valve according to the present invention includes in a following order: an aortic wall incision step where an aortic wall is cut so as to expose an aortic valve side of the inside of an aortic duct to an open atmosphere; an aortic valve forming step where the aortic valve is formed by restricting a distance between commissures disposed adjacently to each other by placing a thread between the plurality of commissures disposed adjacently to each other; and an aortic wall suturing step where the aortic wall cut in the aortic wall incision step is sutured so as to close the aortic wall.

In the method of repairing an aortic valve according to the present invention, a distance between the commissures disposed adjacently to each other (inter-commissure distance) can be restricted by placing the thread between the plurality of commissures disposed adjacently to each other. Accordingly, even when a diameter of the aortic valve in the vicinity of an aortic annulus or an aortic root is expanded in a process where a heart is beating, the enlargement of the inter-commissure distance can be directly prevented due to a tension of the thread.

As described above, according to the present invention, a geometric relationship (a triangular shape, an inter-commissure distance or the like) between a plurality of commissures can be normalized, and the normalized state can be maintained. Accordingly, it is possible to prevent the recurrence of an aortic regurgitation (AR) which is caused by collapsing of the geometric relationship between the commissures.

In the present invention, "commissure" refers to a portion where cusps disposed adjacently to each other abut against each other and are joined to each other. However, "commissure" also includes a portion of a wall or a portion of a tissue of an aortic wall in the vicinity of the above-mentioned portion.

In the method of repairing an aortic valve according to the present invention, it is preferable that in the aortic valve forming step, the distance between the commissures be restricted such that a circumferential length of an imaginary triangle formed by imaginarily joining the commissures at three portions becomes smaller than the circumferential length of the imaginary triangle before an operation by placing the thread between the plurality of the commissures.

With such a configuration, the geometric relationship between the plurality of commissures can be normalized, and the prevention of aortic regurgitation can be improved while maintaining the normalized state.

In the method of repairing an aortic valve according to the present invention, it is preferable that the respective commissures be formed such that the commissures are reinforced using the thread and, thereafter, the thread be placed between the plurality of commissures disposed adjacently to each other.

With such a configuration, it is possible to form an aortic valve where the commissures are reinforced and hence, tissues of the commissures are minimally broken even when a tension of the thread, a fastening strength by the thread or the like changes.

In the method of repairing an aortic valve according to the present invention, it is preferable that one thread be continuously placed between the commissures at three portions thus forming a closed approximately triangle using one thread.

With such a configuration, the geometric relationship between three commissures can be firmly maintained by fixedly restricting a length of the circumference (circumferential length) when the thread makes one turn by joining commissures at three portions.

In the method of repairing an aortic valve according to the present invention, it is preferable that the aortic valve forming step include: a first suturing step where a first commissure is sutured by one end side of the thread; a second suturing step where a second commissure is sutured by the other end side of the thread while the other end side of the thread is pulled; a third suturing step where a third commissure is sutured by the other end side of the thread while the other end side of the thread is pulled; and a fourth suturing step where the other end side of the thread is tied to the one end side of the thread or the first commissure is sutured by the other end side of the thread while the other end side of the thread is pulled.

BRIEF DESCRIPTION OF DRAWINGS

FIG. 5A and FIG. 5B are views for describing the manner of operation and advantageous effects of the method of repairing an aortic valve according to the embodiment 1, wherein

FIG. 8A to FIG. 8C are views showing a state of an aortic valve in a test example, wherein

FIG. 9A and FIG. 9B are photographs showing a state of the aortic valve in the test example, wherein

FIG. 11A to FIG. 11C are views for describing a conventional method of repairing an aortic valve, wherein FIG. 11B and FIG. 11C are views for describing repairing of the valve.

In the above-mentioned drawings, FIG. 2A to FIG. 4B, FIG. 5A, FIG. 5B, and FIG. 7 show a mode where the aortic valve is viewed from a direction substantially perpendicular to an incision surface (cutting surface) when the aortic wall is cut.

DESCRIPTION OF PREFERRED EMBODIMENTS

Hereinafter, a method of repairing an aortic valve according to the present invention is described with reference to embodiments shown in the drawings. Except for photographs, the respective drawings are schematic views, and the drawings do not always strictly reflect actual sizes.

Embodiment 1

1. Configuration of Method of Repairing Aortic Valve According to Embodiment 1

Figure 1:
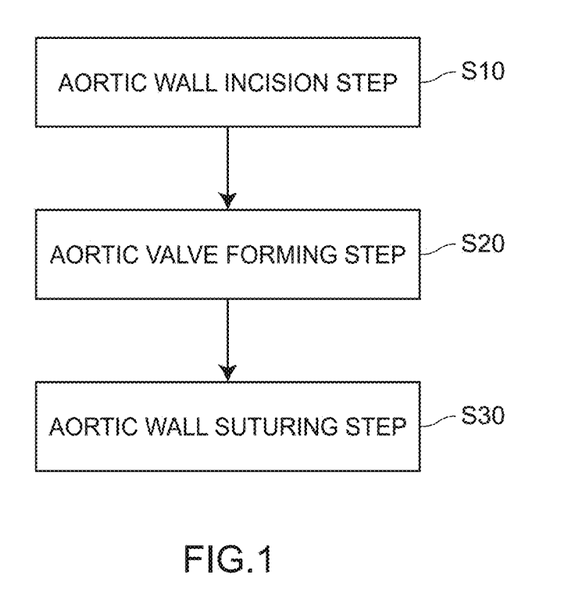
FIG. 1 is a flowchart for describing a method of repairing an aortic valve according to an embodiment 1.

FIG. 1 is a flowchart for describing the method of repairing an aortic valve according to the embodiment 1. As shown in FIG. 1, the method of repairing an aortic valve according to the embodiment 1 includes aortic wall incision step S10, aortic valve forming step S20, and aortic wall suturing step S30 in this order.

(1) Aortic Wall Incision Step S10

Aortic wall incision step S10 is a step where an aortic wall 822 is cut so as to expose an aortic valve 810 side in the inside of an aortic duct 825 to an open atmosphere (see also FIG. 11A).

To be more specific, in aortic wall incision step S10, an aorta 820 is cut by performing incision at a suitable portion of the aorta 820 (for example, incision portion a-a indicated by an arrow in FIG. 11A).

In performing aortic wall incision step S10, a heart 800 is stopped (cardiac arrest). Further, the aorta 820 is shut off by an aortic cross clamp 550 downstream of the incision portion a-a thus terminating an outgoing flow and an incoming flow of blood between an upstream side and a downstream side of the aortic cross clamp 550.

(2) Aortic Valve Forming Step S20

Aortic valve forming step S20 is a step where an aortic valve 810 is repaired by restricting a distance between commissures disposed adjacently to each other by placing a thread 560 between the plurality of commissures disposed adjacently to each other (see FIG. 2A to FIG. 4B).

In such a step, "between a plurality of commissures disposed adjacently to each other" means, to be more specific, between CM1 and CM2, between CM2 and CM3, or between CM3 and CM1.

"placing a thread 560" is also referred to as "connecting" the plurality of commissures disposed adjacently to each other by the thread.

"restricting" means, for example, (a) setting a distance between the commissures (inter-commissure distance) to an appropriate distance by shortening the inter-commissure distance compared to the corresponding distance before an operation or (b) restricting the enlargement of an inter-commissure distance such that it is possible to prevent the enlargement of the inter-commissure distance exceeding the appropriate distance in a process where a heart beats (as opposed to, a case where the inter-commissure distance becomes shorter than the restricted distance temporarily being allowable) or the like.

In the embodiment 1, a suture for suturing is used as "thread 560". However, thread 560 is not limited to a surgical suture for suturing.

Hereinafter, aortic valve forming step S20 is described in detail with reference to FIG. 2A to FIG. 4B.

(2-1) In the Embodiment 1, as Aortic Valve Forming Step S20 the step is performed where the respective commissures are formed so as to reinforce commissures using a thread (commissure reinforcing step) and, then, the step is performed where a thread is placed between the plurality of commissures disposed adjacently to each other (inter-commissure distance restricting step) are performed in this order.

(2-2) Commissure Reinforcing Step

Figure 2A:
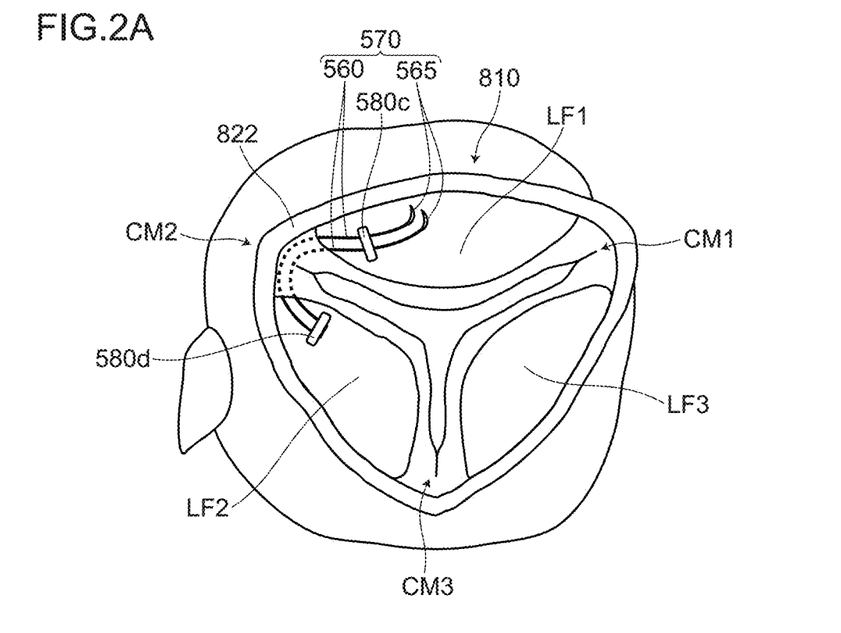
FIG. 2A and FIG. 2B are views for describing the method of repairing an aortic valve according to the embodiment 1, and are views for illustrating a commissure reinforcing step.
Figure 2B:
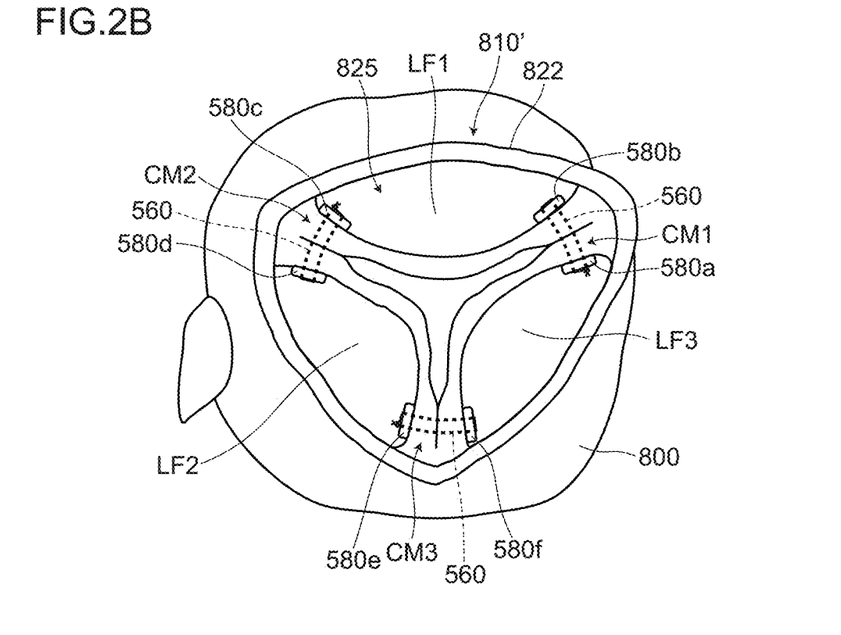

FIG. 2A and FIG. 2B are views for illustrating the commissure reinforcing step.

The commissure reinforcing step is a step for forming the respective commissures in such a manner that the commissures are reinforced using the thread. The commissure reinforcing step may be performed using any method provided that the commissures can be reinforced.

For example, the commissure reinforcing step may be performed by a method substantially equal to "commissure forming step" described previously as the conventional method of repairing an aortic valve.

That is, the case is described hereinafter where "second commissure CM2" where a first cusp LF1 and a second cusp LF2 abut against each other and are joined to each other is formed. Firstly, a double armed suture 570 is made to penetrate a pledget 580d in advance. Then, needles 565 of the double armed suture 570 are made to pierce the second cusp LF2, and the needles 565 and threads 560 are made to penetrate the first cusp LF1. On the first cusp LF1 side, the needles 565 and the threads 560 are made to penetrate another pledget 580c (see FIG. 2A). Then, the threads 560 are tied to each other by fastening on a first cusp LF1 side.

Through such steps, a tissue of the first cusp LF1 on a side close to the second commissure CM2 and a tissue of the second cusp LF2 on a side close to the second commissure CM2 are pulled together while catching a wall portion of the aortic wall 822, and are fixed in a state where the tissues are sandwiched by the pledget 580c and the pledget 580d.

Substantially the same step is performed in the same manner also with respect to "third commissure CM3" where the second cusp LF2 and a third cusp LF3 abut against each other and are joined to each other and "first commissure CM1" where the third cusp LF3 and the first cusp LF1 abut against each other and are joined to each other (see FIG. 2B).

By performing such commissure reinforcing step (formation of commissures), portions in the vicinity of the respective commissures CM1, CM2, and CM3 can be reinforced.

The specific configuration (specific performing method) of the commissure reinforcing step is not limited to the above-mentioned example. For example, the commissure reinforcing step can suitably adopt variations. The commissure reinforcing step may be performed using the pledget 580 only on one side at respective commissures CM1, CM2, and CM3, or the commissure reinforcing step may be performed using only the thread 560 without using the pledget 580, or suturing may be performed at positions or portions different from the above.

(2-3) Inter-Commissure Distance Restricting Step

FIG. 3A, FIG. 3B, FIG. 4A, and FIG. 4B are views for illustrating the inter-commissure distance restricting step. The inter-commissure distance restricting step is a step where a thread is placed between the plurality of the commissures disposed adjacently to each other.

In the embodiment 1, in the inter-commissure distance restricting step, one thread 560 is continuously placed between the commissures CM1, CM2, and CM3 disposed at three portions thus forming a closed approximately triangle using one thread 560.

To be more specific, a first suturing step to a fourth suturing step are performed in the following order. In the first suturing step, the first commissure CM1 is sutured by one end 560a side of the thread 560. In the second suturing step, the second commissure CM2 is sutured by the other end 560b side of the thread 560 while the other end 560b side of the thread 560 is pulled. In the third suturing step, the third commissure CM3 is sutured by the other end 560b side of the thread 560 while the other end 560b side of the thread 560 is pulled. In the fourth suturing step, the other end 560b side of the thread 560 is tied to the one end 560a side of the thread 560 or the first commissure CM1 is sutured by the other end 560b side of the thread 560 while the other end 560b side of the thread 560 is pulled. The details of these suturing steps are described hereinafter.

(a) First Suturing Step

Figure 3A:
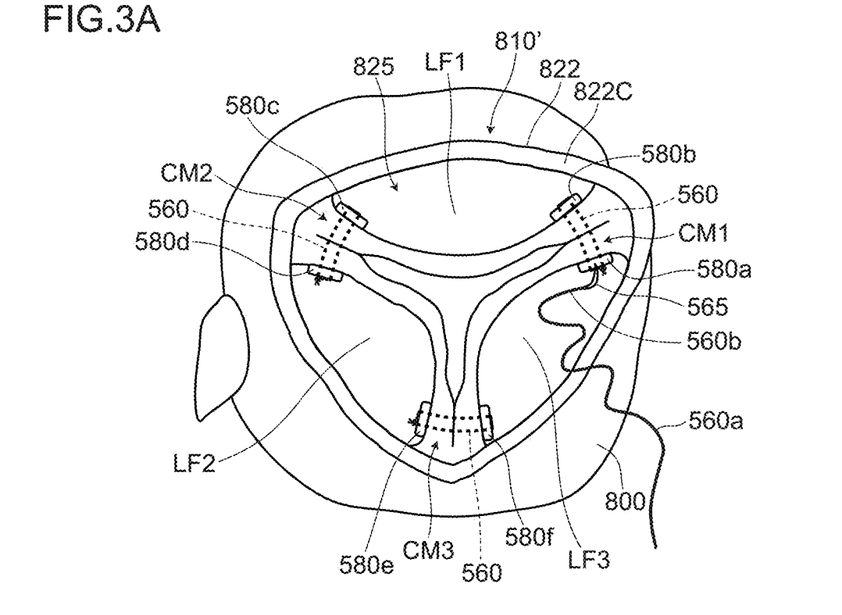
FIG. 3A and FIG. 3B are views for describing the method of repairing an aortic valve according to the embodiment 1, and are views for illustrating an inter-commissure distance restricting step.
Figure 3B:
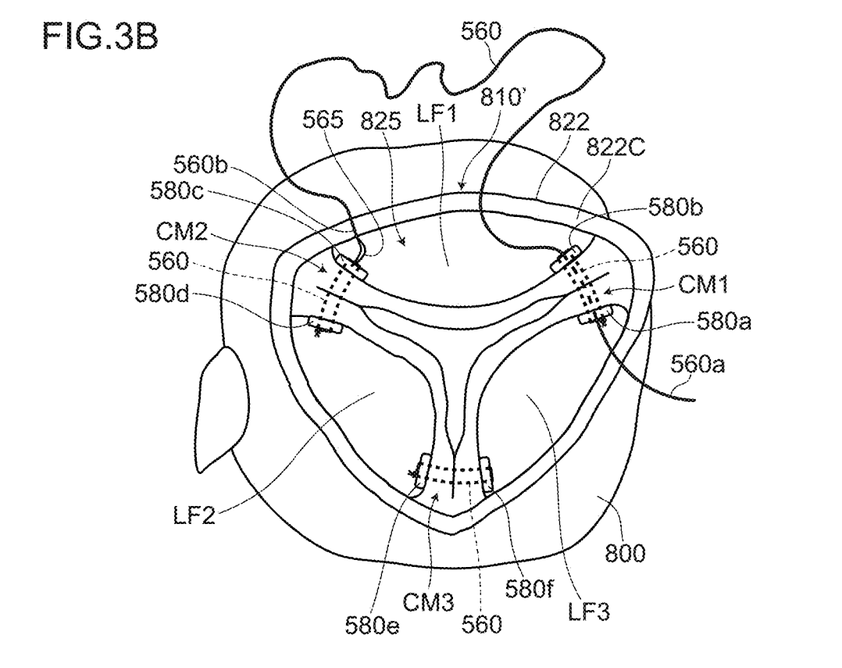

A needle 565 mounted on the other end 560b side is pierced into the pledget 580a disposed in the first commissure CM1 (see FIG. 3A), the needle 565 and the thread 560 are made to penetrate through a tissue in the vicinity of the first commissure CM1 until the needle 565 and the thread 560 reach the pledget 580b disposed on an opposite side, and the first commissure CM1 is sutured by one end 560a side of the thread 560 (the side to which the needle 565 is not mounted) (see FIG. 3B).

(b) Second Suturing Step

Figure 4A:
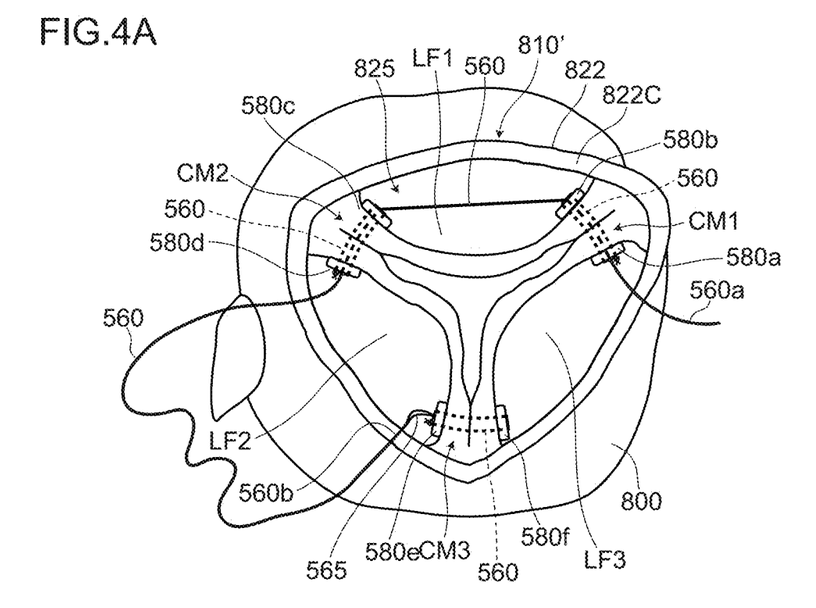
FIG. 4A and FIG. 4B are views for describing the method of repairing an aortic valve according to the embodiment 1, and are views for illustrating the inter-commissure distance restricting step.

Next, the needle 565 is pierced into the pledget 580c disposed in the second commissure CM2 (see FIG. 3B), the needle 565 and the thread 560 are made to penetrate through a tissue in the vicinity of the second commissure CM2 until the needle 565 and the thread 560 reach the pledget 580d disposed on an opposite side, and the second commissure CM2 is sutured by the other end 560b side of the thread 560 (side to which the needle 560 is mounted) while the other end 560b side of the thread 560 is pulled (see FIG. 4A).

(c) Third Suturing Step

Figure 4B:
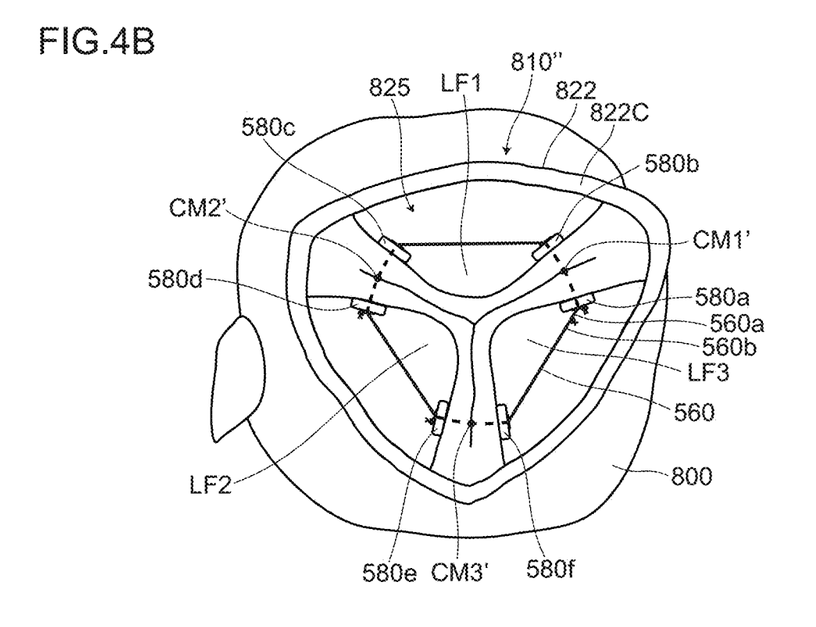

Next, the needle 565 is pierced into the pledget 580e disposed in the third commissure CM3 (see FIG. 4A), the needle 565 and the thread 560 are made to penetrate through a tissue in the vicinity of the third commissure CM3 until the needle 565 and the thread 560 reach the pledget 580f disposed on an opposite side, and the third commissure CM3 is sutured by the other end 560b side of the thread 560 while the other end 560b side of the thread 560 is pulled (see FIG. 4B).

(d) Fourth Suturing Step

The other end 560b side of the thread 560 is tied (fastened) to one end 560a side while the other end 560b side of the thread 560 is pulled such that an imaginary triangle becomes smaller than the imaginary triangle before an operation (see FIG. 4B). Alternatively, the first commissure CM1 is sutured by the other end 560b side of the thread 560 while the other end 560b side of the thread 560 is pulled such that the imaginary triangle becomes smaller than the imaginary triangle before the operation.

In both cases, a predetermined distance is maintained and a tension is maintained between the first commissure and the second commissure, between the second commissure and the third commissure, and between the third commissure and the first commissure respectively.

The commissures at this stage of operation are expressed as a first commissure CM1', a second commissure CM2', and a third commissure CM3' by changing symbols compared to the commissures before the operation (see FIG. 4B).

In the above-mentioned inter-commissure distance restricting step, the distances between the commissures are restricted such that a circumferential length of an imaginary triangle (CM1'-CM2'-CM3') formed by imaginarily joining the commissures at three portions becomes smaller than the circumferential length of the imaginary triangle before an operation (CM1-CM2-CM3) by placing the thread 560 between the plurality of the commissures (between the first commissure and the second commissure, between the second commissure and the third commissure, and between the third commissure and the first commissure).

By performing aortic valve forming step S20 described above, it is possible to obtain more properly formed aortic valve 810" (see FIG. 4B).

(3) Aortic Wall Suturing Step S30

Aortic wall suturing step S30 is a step where the aortic wall 822 cut in the aortic wall incision step S10 is sutured so as to close the aortic wall 822.

2. Advantageous Effects Acquired by Method of Repairing an Aortic Valve According to Embodiment 1

Figure 5A:
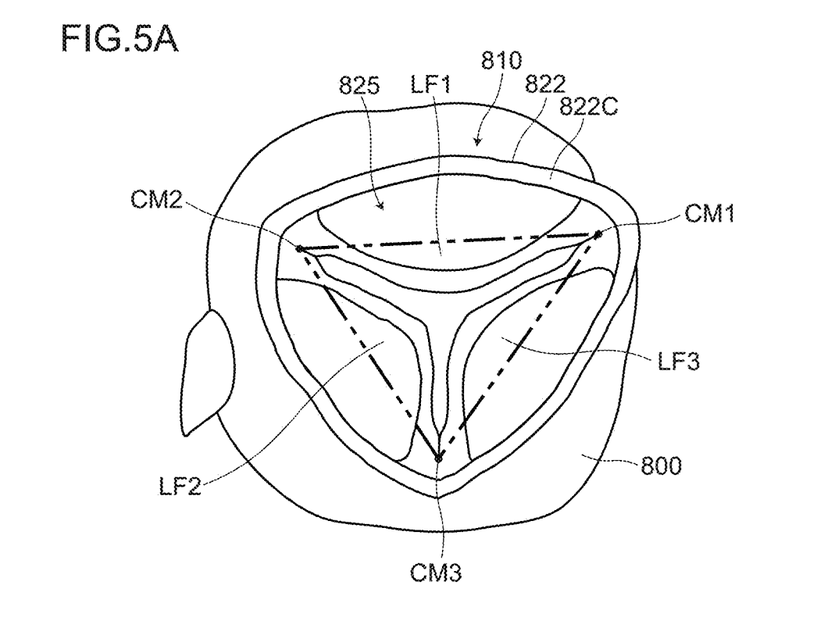
FIG. 5A shows a state of an aortic valve before the method of repairing an aortic valve is performed (also referred to as "before an operation" hereinafter)
Figure 5B:
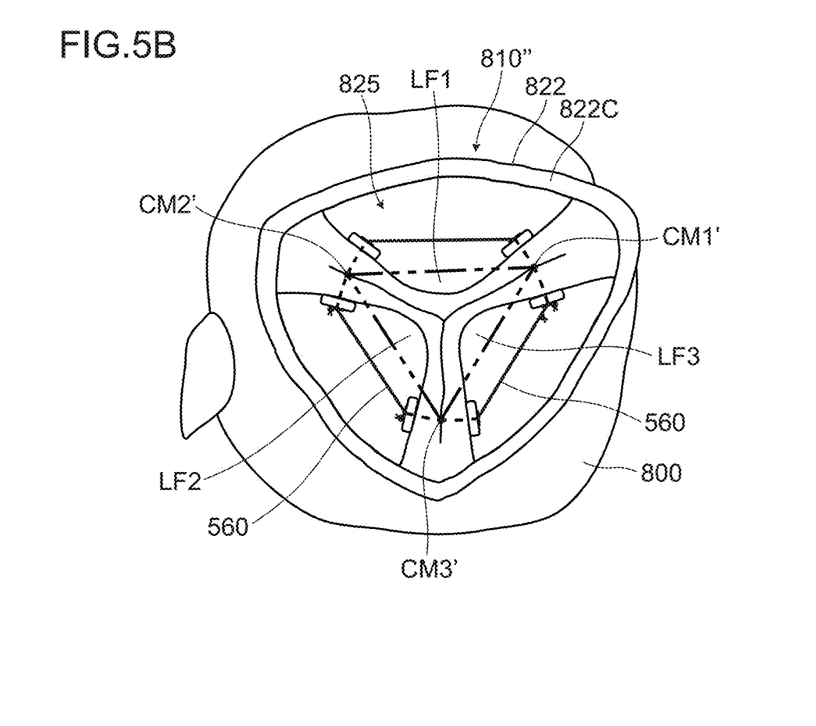
FIG. 5B shows a state of the aortic valve after the method of repairing an aortic valve is performed (also referred to as "after the operation" hereinafter)
Figure 6:
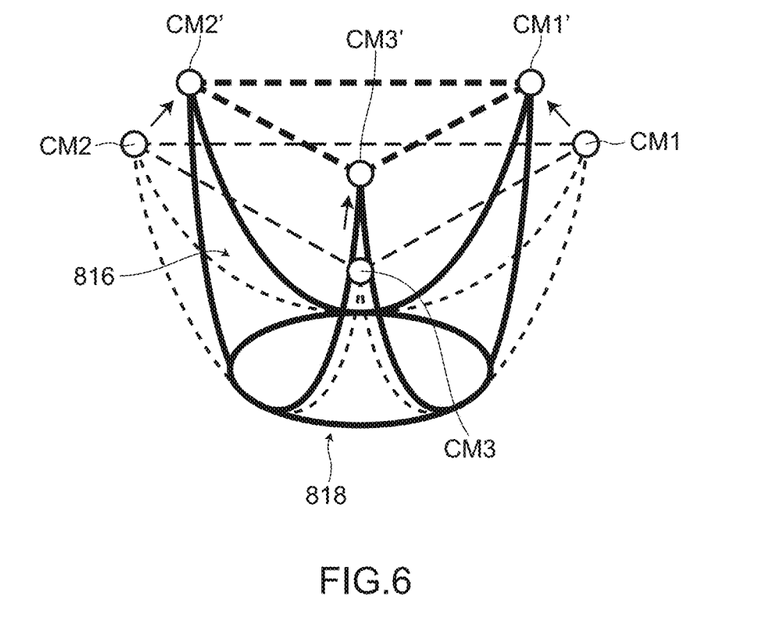
FIG. 6 is a schematic view for describing normalization of a geometric relationship between a plurality of commissures in performing the method of repairing an aortic valve according to the embodiment 1.

FIG. 5A and FIG. 5B are views for describing the manner of operation and advantageous effects of the method of repairing an aortic valve according to the embodiment 1. FIG. 5A shows a state of the aortic valve 810 before an operation, and FIG. 5B shows a state of the aortic valve 810" after the operation. FIG. 6 is a schematic view for describing normalization of a geometric relationship between a plurality of commissures in performing the method of repairing an aortic valve according to the embodiment 1. In the drawing, symbol 816 indicates a triangle of each cusp, and symbol 818 indicates an annulus.

(1) The method of repairing an aortic valve according to the embodiment 1 includes the aortic valve forming step for forming the aortic valve 810" by restricting a distance between the commissures disposed adjacently to each other (inter-commissure distance) by placing the thread between the plurality of commissures disposed adjacently to each other (between the commissures CM1 and CM2, between the commissures CM2 and CM3, and/or between the commissures CM3 and CM1). Accordingly, even when a diameter of the aortic valve in the vicinity of the aortic annulus or an aortic root is expanded in a process where a heart is beating, the enlargement of the inter-commissure distance can be directly prevented due to a tension of the thread (see FIG. 5B).

According to the method of repairing an aortic valve according to the embodiment 1, a geometric relationship (a triangular shape, the inter-commissure distances or the like) between a plurality of commissures (between the commissures CM1 and CM2, between the commissures CM2 and CM3, and/or between the commissures CM3 and CM1) can be normalized, and the normalized state can be maintained. Accordingly, it is possible to prevent the recurrence of an aortic regurgitation (AR) which is caused by collapsing of the geometric relationship between the commissures.

(2) In the method of repairing an aortic valve according to the embodiment 1, in aortic valve forming step S20, the respective commissures CM1, CM2, and CM3 are formed such that the commissures CM1, CM2, and CM3 are reinforced using the thread 560 (commissure reinforcing step), thereafter, the thread is placed between the plurality of commissures disposed adjacently to each other (between the commissures CM1 and CM2, between the commissures CM2 and CM3, and between the commissures CM3 and CM1) (inter-commissure distance restricting step). With such a configuration, it is possible to form an aortic valve 810" where the commissures CM1', CM2', and CM3' are reinforced and hence, tissues of the commissures CM1', CM2', and CM3' are minimally broken even when a tension of the thread 560, a fastening strength by the thread 560 or the like changes.

In the commissure reinforcing step, it is preferable to use the pledgets 580 in addition to the thread 560. The tissues of the commissures CM1, CM2, and CM3 are fixed in a pressed manner by surfaces of the pledgets 580 and hence, it is possible to bring the commissures CM1, CM2, and CM3 into a more firm state.

(3) In the method of repairing an aortic valve according to the embodiment 1, in aortic valve forming step S20, the distances between the commissures are restricted such that a circumferential length of an imaginary triangle (CM1'-CM2'-CM3') formed by imaginarily joining the commissures at three portions (indicating commissures in "narrow meaning" where free edges of the cusps abut against each other in this embodiment 1) becomes smaller than the circumferential length of the imaginary triangle (CM1-CM2-CM3) before an operation by placing the thread 560 between the plurality of the commissures(between the commissures CM1 and CM2, between the commissures CM2 and CM3, and between the commissures CM3 and CM1).

By placing the thread 560 between the commissures in an approximately triangular shape, it is possible to make a circumferential length of an imaginary triangle (CM1'-CM2'-CM3') formed by imaginarily joining commissures (narrow meaning) at three portions after operation (see FIG. 5B) smaller than a circumferential length of an imaginary triangle (CM1-CM2-CM3) before the operation (see FIG. 5A).

Further, as shown in FIG. 6, by placing the thread 560 between the commissures in an approximately triangular shape, the distances between the commissures CM1', CM2', and CM3' (narrow meaning) after the operation can be made smaller than the distances between the commissures CM1, CM2, and CM3 (narrow meaning) before the operation. Further, the positions of the respective commissures can be lifted in an upper direction (assuming that a left ventricle 845 side not shown in the drawing be disposed on a lower side and an incision surface 822C side of the aortic wall 822 be disposed on an upper side), and the respective commissures can be made to approach toward the center of the aortic valve 810 (close to the center of the duct). Further, sizes (diameters) of a Valsalva sinus and a sinotubular junction (STJ) not shown in the drawing can be suppressed to small values.

With such a configuration, according to the method of repairing an aortic valve of the embodiment 1, the geometric relationship between the plurality of commissures CM1', CM2', and CM3' can be normalized, and the prevention of aortic regurgitation can be improved while maintaining the normalized state.

(4) According to the method of repairing an aortic valve of the embodiment 1, in aortic valve forming step S20, one thread 560 is continuously placed between the commissures CM1, CM2, and CM3 at three portions thus forming a closed approximately triangle using one thread 560. With such a configuration, the geometric relationship between three commissures CM1', CM2', and CM3' can be firmly maintained by fixedly restricting also a length of the circumference (circumferential length) when the thread makes one turn by joining commissures CM1', CM2', and CM3' (narrow meaning) at three portions.

Embodiment 2

Figure 7:
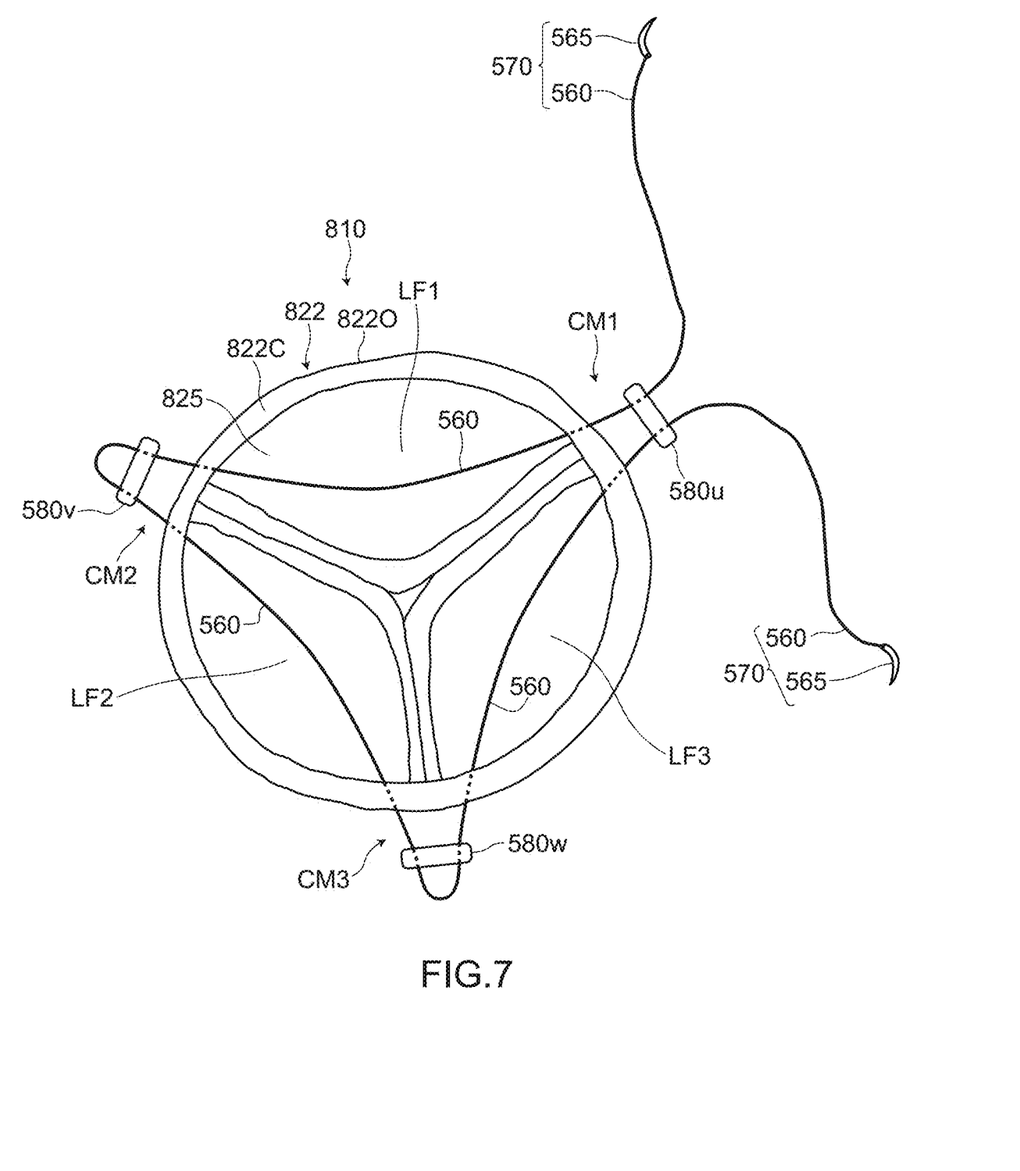
FIG. 7 is an illustrative view for describing a method of repairing an aortic valve according to an embodiment 2.

FIG. 7 is an illustrative view for describing a method of repairing an aortic valve according to an embodiment 2. To be more specific, FIG. 7 is a view showing a mode in the midst of performing an inter-commissure distance restricting step.

The method of repairing an aortic valve according to the embodiment 2 basically has substantially the same configuration as the method of repairing an aortic valve according to the embodiment 1. However, the method of repairing an aortic valve according to the embodiment 2 differs from the method of repairing an aortic valve according to the embodiment 1 with respect to the manner of treating a thread 560 and pledgets 580u to 580w in respective commissures.

As shown in FIG. 7, in the method of repairing an aortic valve according to the embodiment 2, in the inter-commissure distance restricting step, the thread 560 and the pledgets 580u to 580w are treated such that, in a first commissure CM1 to a third commissure CM3 respectively, needles 565 and the thread 560 are made to penetrate an aortic wall 822 such that the needles 565 and the thread 560 reach an outer wall 822O side of the aortic wall 822, and the pledgets 580u to 580w through which the thread 560 passes are disposed at the outer wall 822O side respectively.

With such a method of repairing of an aortic valve, even when a tension of the thread 560 is increased due to beating of a heart, the tension can be received by a tissue on an outer wall 822O side of the aortic wall 822 more robust than a tissue of the inside of an aortic duct 825. Further, the pledgets 580u to 580w disposed on an outer wall 822O side can also absorb the increase of the tension to some extent.

According to the method of repairing an aortic valve of the embodiment 2, a geometric relationship between a plurality of commissures can be normalized in a more robust manner and, at the same time, such a normalized state can be maintained.

Further, according to the method of repairing an aortic valve of the embodiment 2, in inter-commissure distance restricting step, the inter-commissure distances are restricted by suturing the first commissure CM1, the second commissure CM1, and the third commissure CM3 respectively using the needles 565 and the thread 560. In such a state, the pledgets 580u to 580w through which the thread 560 passes are also disposed. That is, by performing the inter-commissure distance restricting step, the commissure reinforcing step can be performed simultaneously.

Accordingly, according to the method of repairing an aortic valve of the embodiment 2, a distance between the commissures can be restricted without additionally performing the commissure reinforcing step as an independent step. Accordingly, an aortic valve can be efficiently repaired.

The method of repairing an aortic valve according to the embodiment 2 has basically substantially the same configuration as the method of repairing an aortic valve according to the embodiment 1 except for the manner of treating the thread 560 and the pledgets 580u to 580w in the respective commissures. Accordingly, the method of repairing an aortic valve according to the embodiment 2 acquires the corresponding advantageous effects found amongst all advantageous effects which the method of repairing an aortic valve according to the embodiment 1 acquires.

Test Example

Inventors of the present invention who are doctors have confirmed that the desired manner of operation and advantageous effects can be acquired by performing the method of repairing an aortic valve according to the embodiment 1. Hereinafter, the confirmed result is introduced in the form of a test example.

1. Aortic Valve 810 Before Operation

Figure 8A:
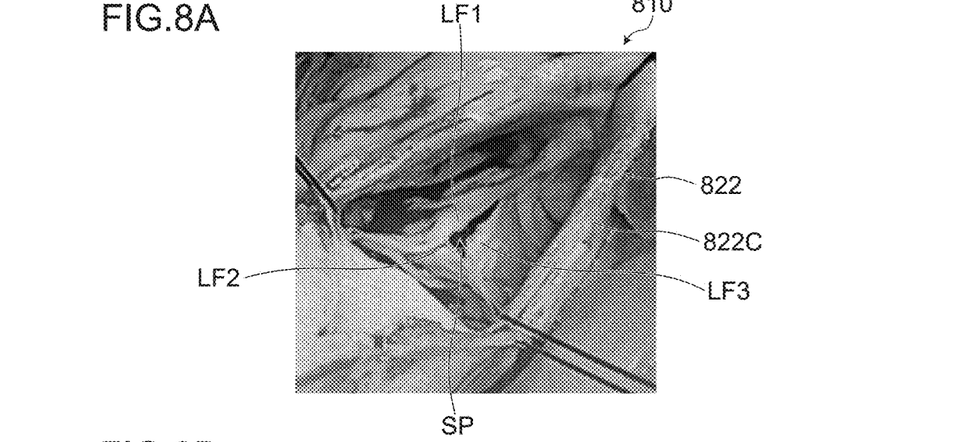
FIG. 8A is a photograph showing a state of the aortic valve 810 before an operation.

FIG. 8A is a photograph showing a state of an aortic valve 810 before an operation. With respect to the description relating to the symbols which appear in the drawing but are not described in the following description, the description of the symbols described with reference to FIG. 1A to FIG. 6 heretofore can be directly used.

The aortic valve 810 according to the test example has a portion where cusps LF1, LF2, and LF3 are not joined to each other due to sinotubular junction (STJ) expansion before an operation (gap SP being formed in the vicinity of the center of the aortic valve 810), and an aortic regurgitation of an intermediate level has occurred (see FIG. 8A).

2. Commissure Reinforcing Step in Aortic Valve Forming Step S20

Figure 8B:
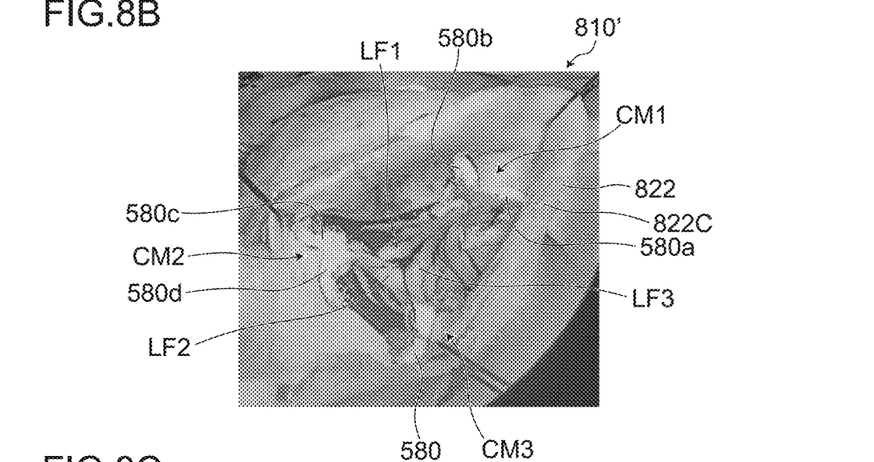
FIG. 8B is a photograph showing a state of the aortic valve after a commissure reinforcing step in aortic valve forming step S20 is performed.

FIG. 8B is a photograph showing a state of the aortic valve after a commissure reinforcing step in aortic valve forming step S20 is performed.

Firstly, the commissure reinforcing step was performed with respect to the aortic valve 810 before an operation. To be more specific, using the method substantially equal to the method described above with reference to FIG. 2A and FIG. 2B, commissures CM1, CM2, and CM3 at three portions were reinforced using a thread (not shown in the drawing by a symbol) and pledgets 580a to 580f (see FIG. 8B).

By such an operation, an aortic valve 810' in a state shown in FIG. 8B was obtained. The pledget 580f was concealed by a tissue so that the pledget 580f did not appear in the photography.

3. Inter-Commissure Distance Restricting Step in Aortic Valve Forming Step S20

Figure 8C:
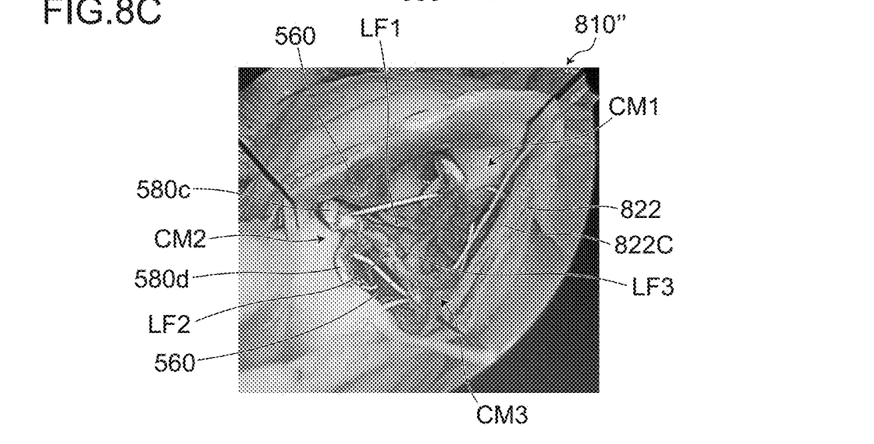
FIG. 8C is a photograph showing a state of the aortic valve after an inter-commissure distance restricting step in aortic valve forming step S20 is performed.

FIG. 8C is a photograph showing a state of the aortic valve after the inter-commissure distance restricting step in aortic valve forming step S20 was performed.

The inter-commissure distance restricting step was performed with respect to the aortic valve 810' on which the commissure reinforcing step was performed. To be more specific, in accordance with a method substantially equal to the method performed through the first suturing step to the fourth suturing step described previously, one thread 560 was continuously placed between the commissures CM1, CM2, and CM3 at three portions (see FIG. 8C).

By such an operation, as shown in FIG. 8C, the aortic valve 810" in a state where a closed approximately triangle is formed using one thread 560 was obtained. The pledgets 580e, 580f were concealed in the tissues and hence, the pledgets 580e, 580f did not appear in the photograph.

4. Advantageous Effects Acquired by Method of Repairing Aortic Valve According to Embodiment 1

Figure 9A:
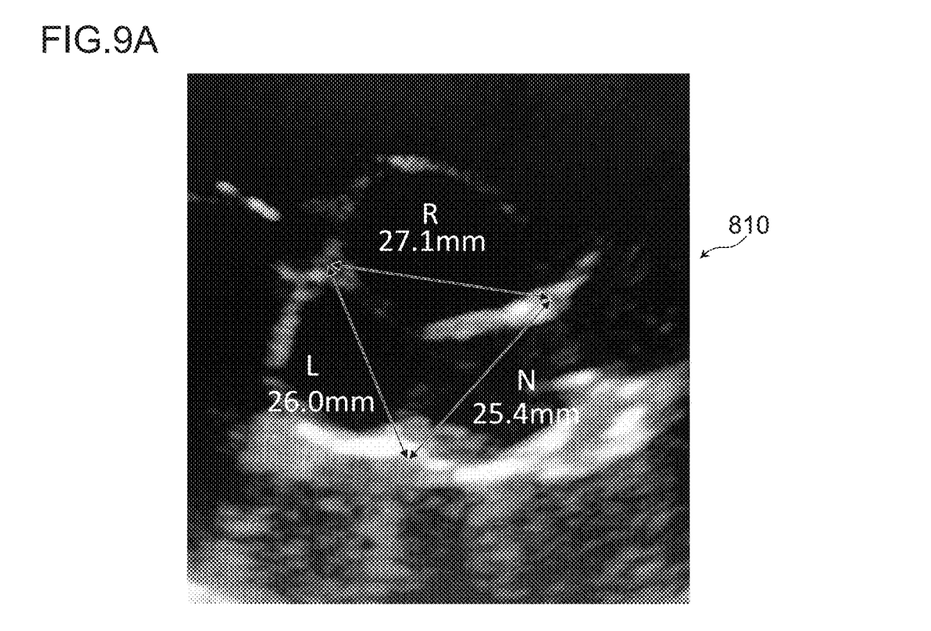
FIG. 9A is an echocardiographic photograph showing a state of the aortic valve before the operation.
Figure 9B:
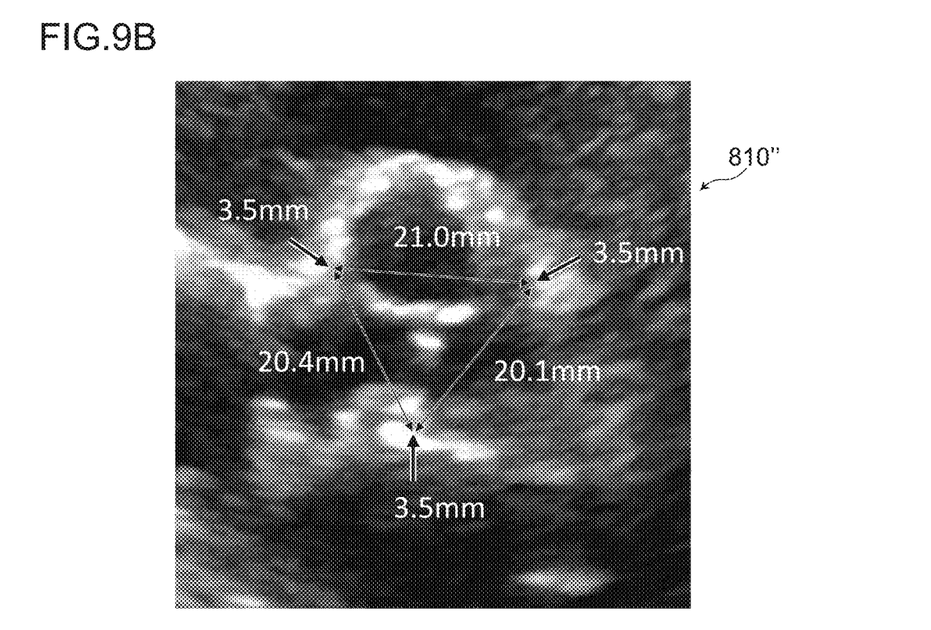
FIG. 9B is an echocardiographic photograph showing a state of the aortic valve after the operation.

FIG. 9A is an echocardiographic photograph showing a state of the aortic valve 810 before the operation. FIG. 9B is an echocardiographic photograph showing a state of the aortic valve 810" after the operation. Symbols corresponding to the respective commissures are not described in FIG. 9A and FIG. 9B.

As shown in FIG. 9A, in the aortic valve 810 before the operation, a distance R between the first commissure CM1 and the second commissure CM2 was 27.1 mm, a distance L between the second commissure CM2 and the third commissure CM3 was 26.00 mm, and a distance N between the third commissure CM3 and the first commissure CM1 was 25.4 mm.

As shown in FIG. 9B, in the aortic valve 810" after the operation (after the method of repairing an aortic valve according to the embodiment 1 was performed), the distance R between a first commissure CM1' and a second commissure CM2' was 21.0 mm, the distance L between the second commissure CM2' and a third commissure CM3' was 20.4 mm, and the distance N between the third commissure CM3' and the first commissure CM1' was 20.1 mm.

In this manner, all inter-commissure distances R, L, and N were shortened and were restricted.

It was confirmed that, along with shortening of the above-mentioned inter-commissure distances, the first commissure CM1 was shifted toward the inside of the aortic valve 810 by 3.5 mm, and the second commissure CM2 and the third commissure CM3 were also respectively shifted to the inside of the aortic valve 810 by 3.5 mm.

From the above, it was confirmed that the geometric relationship between the plurality of commissures was normalized.

It was confirmed that the free edges of the cusps LF1, LF2, and LF3 were tightly joined to each other due to the above-mentioned normalization of the geometric relationship between the plurality of commissures. Further, it was also confirmed that the inter-commissure distances were maintained by the tension of the thread 560 and hence, joining of the cusps LF1, LF2, and LF3 were also ensured.

As has been described heretofore, it was confirmed that, according to the method of repairing an aortic valve according to embodiment 1, the geometric relationship (triangular shape, inter-commissure distances or the like) between the plurality of commissures can be normalized and the normalized state can be maintained.

Modification

The present invention has been described heretofore based on the above-mentioned respective embodiments. However, the present invention is not limited to the above-mentioned respective embodiments. The present invention can be carried out in various modes without departing from the gist of the present invention, and the following modifications are also conceivable, for example.

(1) The numbers, materials, shapes, positions, sizes and the like of the constitutional elements described in the above-mentioned respective embodiments are only provided for an exemplifying purpose, and these factors can be changed within a range that advantageous effects of the present invention are not impaired.

(2) In the respective embodiments, in the commissure reinforcing step (see FIG. 2A and FIG. 2B), the first suturing step to the third suturing step are performed in a mode where the thread 560 passes straight through the respective commissures CM1, CM2, and CM3 directly. However, the present invention is not limited to such operations.

The first suturing step to the third suturing step are performed in a mode where when the commissure (either one of commissures CM1, CM2, or CM3) is sutured by the thread 560, the thread 560 is fastened each time at the commissure (so-called anchoring).

Figure 10A:
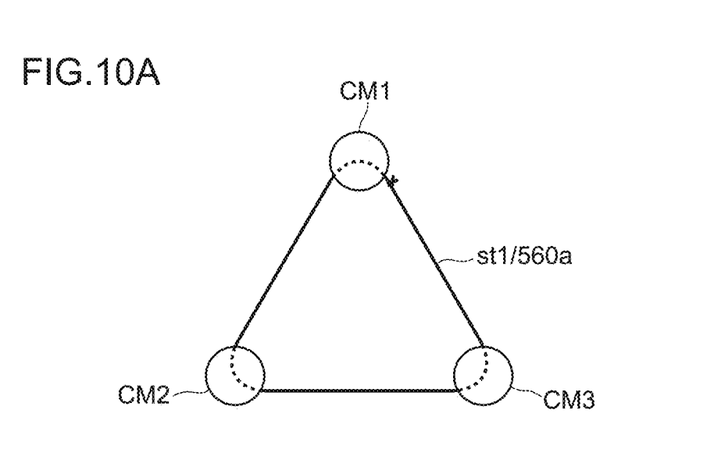
FIG. 10A to FIG. 10C are schematic views showing variations of placing threads in an inter-commissure distance restricting step.

(3) In the respective embodiments, the method is adopted where, in the aortic valve forming step, one thread is continuously placed between the commissures at three portions thus forming a closed approximately triangle using one thread (see FIG. 10A). However, the present invention is not limited to such a method.

Figure 10B:
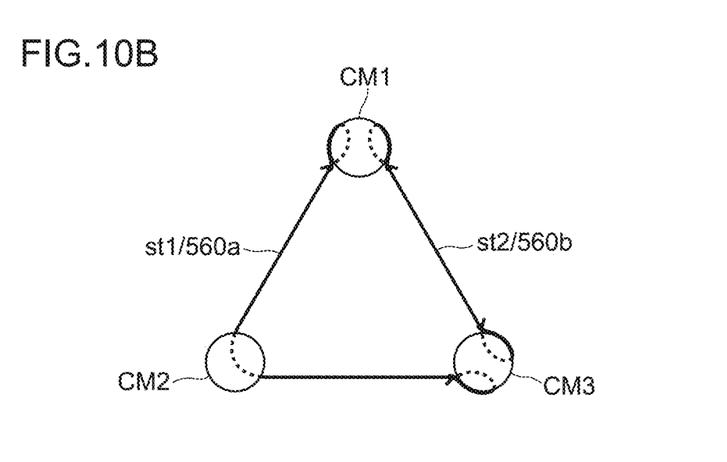
Figure 10C:
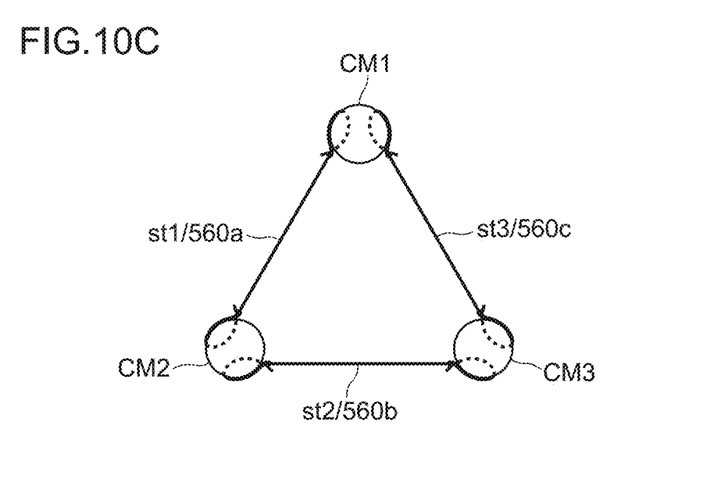

FIG. 10A to FIG. 10C are schematic views showing variations of placing a thread 560 in an inter-commissure distance restricting step.

For example, as shown in FIG. 10B, two different threads st1/560a and st2/560b may be placed between commissures. To be more specific, a method may be adopted where the first thread st1/560a is continuously placed between the first commissure CM1 and the second commissure CM2 and between the second commissure CM2 and the third commissure CM3, and the second thread st2/560b is placed between the third commissure CM3 and the first commissure CM1 (see FIG. 10B). Further, as shown in FIG. 10C, three different threads st1/560a, st2/560b, and st3/560c may be placed between the commissures. To be more specific, a method may be adopted where the first thread st1/560a is placed between the first commissure CM1 and the second commissure CM2, the second thread st2/560b is placed between the second commissure CM2 and the third commissure CM3, and the third thread st3/560c is placed between the third commissure CM3 and the first commissure CM1.

(4) In the respective embodiments, in the aortic valve forming step, firstly, the commissure reinforcing step (so-called forming of the commissures) is performed and, thereafter, the inter-commissure distance restricting step is performed. However, the present invention is not limited to such steps. Depending on cases, the inter-commissure distance restricting step may be performed directly while omitting the commissure reinforcing step (forming of the commissures).

What is claimed is:

1. A method of repairing an aortic valve comprising in a following order:
   an aortic wall incision step where an aortic wall is cut so as to expose an aortic valve side in the inside of an aortic duct to an open atmosphere;
   an aortic valve forming step where the aortic valve is formed by restricting a distance between commissures disposed adjacently to each other by placing a thread between the plurality of commissures disposed adjacently to each other; and
   an aortic wall suturing step where the aortic wall cut in the aortic wall incision step is sutured so as to close the aortic wall.

2. The method of repairing an aortic valve according to claim 1, wherein in the aortic valve forming step, the distance between the commissures is restricted such that a circumferential length of an imaginary triangle formed by imaginarily joining the commissures at three portions becomes smaller than the circumferential length of the imaginary triangle before an operation by placing the thread between the plurality of the commissures.

3. The method of repairing an aortic valve according to claim 2, wherein in the aortic valve forming step, the respective commissures are formed such that the commissures are reinforced using the thread and, thereafter, the thread is placed between the plurality of commissures disposed adjacently to each other.

4. The method of repairing an aortic valve according to claim 3, wherein in the aortic valve forming step, one thread is continuously placed between the commissures at three portions thus forming a closed approximately triangle using one thread.

5. The method of repairing an aortic valve according to claim 4, wherein the aortic valve forming step includes:
   a first suturing step where a first commissure is sutured by one end side of the thread;
   a second suturing step where a second commissure is sutured by the other end side of the thread while the other end side of the thread is pulled;
   a third suturing step where a third commissure is sutured by the other end side of the thread while the other end side of the thread is pulled; and
   a fourth suturing step where the other end side of the thread is tied to the one end side of the thread or the first commissure is sutured by the other end side of the thread while the other end side of the thread is pulled.

* * * * *